(12) United States Patent
Leal et al.

(10) Patent No.: US 10,820,926 B1
(45) Date of Patent: Nov. 3, 2020

(54) UTERINE MANIPULATION DEVICE

(71) Applicants: José Gerardo Garza Leal, San Pedro Garza Garcia (MX); José Gerardo Garza Marichalar, Monterrey (MX)

(72) Inventors: José Gerardo Garza Leal, San Pedro Garza Garcia (MX); José Gerardo Garza Marichalar, Monterrey (MX)

( * ) Notice: Subject to any disclaimer, the term of this patent is extended or adjusted under 35 U.S.C. 154(b) by 0 days.

(21) Appl. No.: 16/588,214

(22) Filed: Sep. 30, 2019

(51) Int. Cl.
*A61B 17/42* (2006.01)
*A61B 17/00* (2006.01)

(52) U.S. Cl.
CPC .. *A61B 17/4241* (2013.01); *A61B 2017/0042* (2013.01); *A61B 2017/00283* (2013.01); *A61B 2017/00389* (2013.01); *A61B 2017/4216* (2013.01)

(58) Field of Classification Search
CPC ................ A61B 17/42; A61B 17/4241; A61B 2017/4216; A61B 2017/4225; A61B 17/0218; A61B 2017/00557; A61B 18/1485; A61B 17/12099; A61B 2017/00805; A61B 1/303; A61B 17/12136; A61B 2018/00559; A61B 2017/4233; A61B 2090/3614; A61B 17/2812; A61B 2090/306; A61B 17/00234; A61B 10/0291; A61B 5/435
See application file for complete search history.

(56) References Cited

U.S. PATENT DOCUMENTS

| | | | |
|---|---|---|---|
| 3,877,433 A | 4/1975 | Librach | |
| 3,948,270 A | 4/1976 | Hasson | |
| 5,209,754 A | 5/1993 | Ahluwalia | |
| 5,382,252 A | 1/1995 | Failla et al. | |
| 5,394,863 A | 3/1995 | Sanford et al. | |
| 5,409,496 A | 4/1995 | Rowden et al. | |
| 5,487,377 A | 1/1996 | Smith et al. | |
| 5,540,700 A | 7/1996 | Rowden et al. | |
| 5,645,561 A * | 7/1997 | Smith ................ | A61B 17/4241 606/193 |
| 5,662,676 A | 9/1997 | Koninckx | |
| 5,840,077 A | 11/1998 | Rowden et al. | |
| D667,550 S | 9/2012 | Keckstein | |
| 2001/0021854 A1 | 9/2001 | Donnez et al. | |
| 2010/0280524 A1 | 11/2010 | Lopez Zepeda | |
| 2010/0305578 A1 | 12/2010 | Auerbach et al. | |
| 2012/0323079 A1* | 12/2012 | Bakare ............... | A61B 1/00066 600/204 |
| 2013/0023896 A1 | 1/2013 | Quimby | |
| 2013/0345714 A1 | 12/2013 | Blair et al. | |
| 2014/0276916 A1 | 9/2014 | Ahluwalia et al. | |
| 2015/0005780 A1 | 1/2015 | Einarsson | |
| 2015/0148812 A1 | 5/2015 | Ahluwalia | |
| 2016/0100861 A1 | 4/2016 | Parys et al. | |
| 2016/0100862 A1 | 4/2016 | Parys | |
| 2017/0189065 A1 | 7/2017 | Einarsson | |

(Continued)

FOREIGN PATENT DOCUMENTS

| | | |
|---|---|---|
| CA | 2840203 | 12/2012 |
| EP | 2666423 | 11/2013 |

(Continued)

*Primary Examiner* — Katherine M Shi
(74) *Attorney, Agent, or Firm* — Levine Bagade Han LLP

(57) ABSTRACT

A uterine manipulator device useful for laparoscopic hysterectomy procedures or other minimally-invasive gynecologic procedures.

19 Claims, 9 Drawing Sheets

(56) References Cited

U.S. PATENT DOCUMENTS

| | | |
|---|---|---|
| 2017/0189066 A1 | 7/2017 | Parys et al. |
| 2017/0333079 A1 | 11/2017 | Ahluwalia et al. |
| 2019/0223912 A1 | 7/2019 | Einarsson |
| 2019/0254708 A1 | 8/2019 | Wu et al. |

FOREIGN PATENT DOCUMENTS

| | | |
|---|---|---|
| WO | WO 2008/100125 | 8/2008 |
| WO | WO 2010/151429 | 12/2010 |

* cited by examiner

UTERINE MANIPULATION DEVICE

CROSS-REFERENCE TO RELATED APPLICATIONS

This application is a nonprovisional of Mexico patent application no. MX/u/2019/000324, filed Jul. 5, 2019, the entirety of which is incorporated by reference.

FIELD OF THE INVENTION

The invention described herein refers, in general, to the field of surgical devices, and more concretely, the invention refers to an improvement of a uterine manipulator device useful for laparoscopic hysterectomy procedures or other minimally-invasive gynecologic procedures. Those skilled in the art will recognize that while the methods and devices described in this application are useful as uterine manipulation devices, the methods and devices have applicability with other organs, including but not limited to organs within the abdominal cavity, the abdominopelvic cavity, and/or any cavity within the body that contains organs.

BACKGROUND OF THE INVENTION

Uterine manipulators are medical instruments that physicians use to manipulate (e.g., move, reposition, or adjust) a patient's uterus during a medical procedure. Such procedures include, but are not limited to, laparoscopic gynecologic surgery, e.g., total laparoscopic hysterectomy (TLH) surgery.

These instruments include a proximal handle that usually remains external to the patient's body during use and a distal or working portion that is inserted into the patient's body. The handle typically provides for manipulation of the instrument during use while the working portion often includes removable components, such as tips and cup structures, that are sized to be inserted into and/or engage a uterus. Typically, the procedure includes sizing of the uterine cavity and/or other organs to determine the specific tip and/or cup size to use. Proper sizing is desired to avoid unintentional perforation of the uterus from within the uterine cavity. Generally, a physician advances the working end of the manipulator through a vaginal cavity and into the uterus. Once the working end positioned within a uterus, the uterus can be manipulated through surgeon or physician-controlled movements of the handle. Following completion of a procedure, the instrument is removed from the patient's body via the vaginal cavity.

The use of uterine manipulation devices is often combined with minimally invasive procedures such as laparoscopy, which is a surgical technique that allows a physician to visualize the inside of the abdomen for diagnosis or for performing surgery. Laparoscopy involves one or more small incisions to access a body cavity, in the case of the uterus the abdominopelvic cavity. The incisions can be made in the abdominal wall for advancing cameras, forceps, knives, and/or other small devices allow the manipulation of abdominal and pelvic organs without completely opening the abdomen.

Gynecological laparoscopy or minimally invasive gynecological surgery is a way to operate a gynecological problem without opening the abdomen. Laparoscopy is a technique that is used more often, not only in gynecology but also in all medical specialties. It provides less time in postoperative recovery, less pain, and a lower rate of surgical complications.

In the case of laparoscopic surgery, a diverse range instruments can be inserted through a number of small incisions made in the lower part of the abdomen. More particularly, in laparoscopic hysterectomy, in addition to a camera, a cutting instrument is inserted into the abdominal cavity through these incisions, which are performed in the iliac fossa. A physician will then use a clamp to maintain the organ, in this case the uterus, in position.

For this type of surgery, a physician inserts a uterine manipulator into the uterus through the vagina. The use of the uterine manipulator is essential to guarantee adequate mobilization of the uterus allowing, for example: anteversion, retroversion, lateral movement, and elevation of the uterus; identification and delimitation of the anterior and posterior folds and the lateral fundi; and visualization of the uterine artery and its isolation in relation to the ureter.

There are a number of conventional uterine manipulation devices described in U.S. Pat. Nos. 3,926,192; 4,000,743; 4,976,717, and 4,997,419. These patents generally describe medical instruments that is inserted into the vagina and passed through the cervix for introduction into the uterus. Some conventional devices provide a cup-shaped member whose end wall is connected to a vacuum source; the cup-shaped member can include a conical element designed for placement against the cervical os.

A Clermont Ferrand model is a well-known uterine manipulator, which allows uterus manipulation and can be adjusted according to the anatomic particularities of the patient using inserts of various sizes. It has lock-in positions between 0° and 90° and a special sealing system that impedes the release of distension gas after opening the vaginal fornix.

However, conventional uterine manipulators do not address the problem of the difficulty and time necessary to separate the uterus and cervix from the vagina during total laparoscopic hysterectomy. For example, these devices require the use of both hands to manipulate the device while adjusting a positioning of the working end (one hand to hold the base or shaft, and another hand to turn a screw or compress a lever to perform articulation).

Therefore, in surgical techniques, there is a real and unsatisfied demand for a device for a simplified total laparoscopic hysterectomy that can reduce the surgical procedure time, minimize blood loss during surgery, minimize the risk of infection and patient lesion during surgery, and minimize anesthesia time. The improved device should offer improved control and handling of the device from outside of the body as the working end of the device manipulates tissues and/or organs within the body.

BRIEF SUMMARY OF THE INVENTION

The illustrations and variations described herein are meant to provide examples of the methods and devices of the invention. It is contemplated that combinations of aspects of specific embodiments or combinations of the specific embodiments themselves are within the scope of this disclosure.

While the inventions described herein are defined by the claim, generally, the methods and devices described herein provide an improvement of existing uterine manipulators, by providing the addition of a rectal probe as an accessory to a uterine manipulator. In variations of the methods and devices, this rectal probe has an illumination source on its tip, which can assist the surgeon during performance of the procedure since the illumination source permits correct identification of the rectum, which is translucid, and if it is not identified properly during surgery can be perforated. This rectal probe can have different sizes to reach the deepest part of the rectum without lesions or perforation. Also, the rectal probe can move along four axes while being adjusted from outside of the body before and/or during the procedure.

The manipulation devices and methods described herein can include a cup structure at the working end that adjusts around the cervix. In variations of the devices, this cup can range in movement of 180°; which allows movement of the uterus in an anteroposterior plane. Variations of the devices and methods can facilitate movement through an actuator installed in the upper portion of a handle. The positioning of the actuator allows for a physician to grasp a stock or grasping portion of a handle and use a thumb or a digit to manipulate the cup structure. Variations of the devices and methods include a colpotomizer as a cup structure, but the invention is not limited to such devices. The actuator can be a wheel structure and/or a geared wheel structure (such as a cogwheel) that engages a gear assembly coupled to the handle.

The cup structure can include a tip structure that, when positioned in the uterus crosses the external and internal cervical os and allows movement of the uterus Likewise, it is beneficial that the device includes the capability to affix cups and tips to accommodate varying sizes of organs for various patients. For example, the various several cup sizes and tips depending on the size of the uterus, cups can include, but are not limited to cup sizes: 30-thirty, 40-forty and 45-forty-five millimeter (i.e., the diameter of the cup. Tip and 3 tip sizes: 5-five, 6-six, and 7-seven centimeters. Any of the tips can include lumens for delivery of fluids (e.g., a contrast agent or saline) as well as balloons to assist in securing the uterus for manipulation.

Variations of the devices of the present disclosure include the ability to deliver a contrast agent for chromotubation (also known as chromopertubation. The passage of the contrast material assists the medical caregiver to determine permeability of the Fallopian tubes exists or not in patients who are being operated on because of infertility.

The methods and devices described herein provide for a uterine manipulator that facilitates laparoscopic hysterectomy procedures, specifically, providing considerable support of greater visualization of internal structures of the human body with a wide range of movement of the manipulator of 180°, being careful, using the light source provided on the tip of the rectal probe, to not perforate the rectum. Also, the methods and devices provide a surgeon with the function to detect causes of infertility by having a chromotubation cannula that allows, through the tunnel of contrast material, observation of Fallopian tube permeability.

In view of the above, the present disclosure includes methods and devices regarding a uterine manipulator. For example, such a device can include a shaft having a far-portion, a near-portion, and a mid-portion extending therebetween, the shaft having a main axis; a handle assembly comprising a housing and a grip portion, the housing coupled in axial alignment to the near portion of the shaft, where the grip portion extends radially away from the housing; an articulating segment coupled to the far portion of the shaft; a gearing assembly located within the handle assembly and coupled to the articulating segment, wherein actuation of the gearing assembly causes articulation of the articulating segment; a cup structure having an open end located distally to a closed end, the closed end removably attached to the articulating segment; a tip assembly coupled to the articulating segment and extending distally through the cup structure; and an actuator coupled to the grip portion and spaced from the housing, the actuator engaged with the gearing assembly such that when a hand of a user grips the grip portion, a thumb or a digit of the hand can rotate/move the actuator causing the gearing assembly to articulate the articulating segment, the cup, and the tip assembly away from the main axis, and where the spacing of the actuator from the main handle permits single handed adjustment of the articulating segment, the cup, and the tip assembly while holding the grip portion.

Variations of the device can further include a balloon device positioned at a far portion of the shaft for sealing the cavity opening.

Additional variations of the device can further include a rectal probe adjustably coupled to the housing of the handle assembly such that manipulation of the grip portion allows manipulation of the rectal probe. The rectal probe can be adjustable axially and rotationally relative to the main housing. The rectal probe can also be angularly adjustable relative to the main axis of the shaft.

In variations of the device, the rectal probe comprises an illumination source at a distal end.

The gearing assembly can be configured to articulate the articulating segment within an arc of at least 180 degrees relative to the main axis.

In variations of the device, tip assembly comprises a lumen to permit delivery of a fluid through the tip assembly. The distal end of the tip assembly can be open and/or the tip assembly can have one or more openings in a sideway to allow fluid to flow therethrough.

In another variation the uterine manipulator further includes a fluid port in fluid communication with the lumen, wherein the fluid port is coupled to a source lumen that is configured to fluidly couple to a fluid supply. The fluid supply can be a contrast fluid, a flushing agent, and/or therapeutic fluids.

The devices can further include a plurality of cup structures of varying sizes, where each of the cup structures is removably coupleable to the articulating segment.

In one variation, the grip portion forms an angle of 180 degrees relative to the main axis. The grip portion can further include an actuator that is a wheel structure or a cogwheel. Variations include a configuration where the wheel structure is rotatable in a plane containing the main axis of the shaft. Alternatively, the wheel structure is rotatable in a plane offset from a plane containing the main axis.

The present disclosure also includes methods of manipulating an organ within a body cavity by a caregiver. For example, one such method includes providing a manipulation device having a handle assembly comprising a housing and a grip portion, the housing coupled in axial alignment a shaft, where the grip portion extends radially away from the housing, the shaft having a tip assembly pivotally coupled to an end of the shaft; manipulating the grip portion to advance the tip assembly into an internal organ cavity of the organ through an opening in the organ; seating a cup structure located on the tip assembly against a wall of the organ surrounding the opening; manipulating the organ by rotating an actuator coupled to the grip portion and spaced from the housing such that a hand of the caregiver can grasp the grip portion while using a thumb or digit of the hand to rotate the actuator, where movement of the actuator permits articulation of the tip assembly to produce movement of the organ within the body cavity.

The method can further include inflating a sealing balloon within the body but external to the internal organ cavity prior to manipulating the organ. For example, inflating a distal balloon within the internal organ cavity occurs prior to manipulating the organ.

The method can also include delivering a contrast agent into the internal organ cavity through the tip assembly.

A variation of the method includes a probe that is affixed to the housing of the handle assembly, wherein manipulating the grip portion also advances the probe into a body opening. The probe can be used to provide illumination.

The organ can comprise an organ selected from the group consisting of a vagina, a uterus, and a rectum.

DESCRIPTION OF THE DRAWINGS

Each of the following figures diagrammatically illustrates aspects of the invention. Variation of the invention from the aspects shown in the figures is contemplated.

DETAILED DESCRIPTION

It is understood that the examples below discuss uses of the manipulation device for uterine manipulation. However, unless specifically noted, variations of the device and method are not limited to use only to manipulate a uterus, instead, the device can be used for general surgical procedures to manipulate organs as needed where the organ is located within a larger cavity within the body. Therefore, the methods and device will have applicability in various parts of the body under any minimally invasive or invasive procedure. Moreover, the invention may be used in any procedure where the benefits of the method and/or device are desired. Furthermore, because it is impractical to display each and every combination of features and aspects of various embodiments, it is understood that where possible, every aspect or feature of an embodiment of the methods and/or devices can be combined with alternate embodiments of methods and/or devices.

Figure 1A:
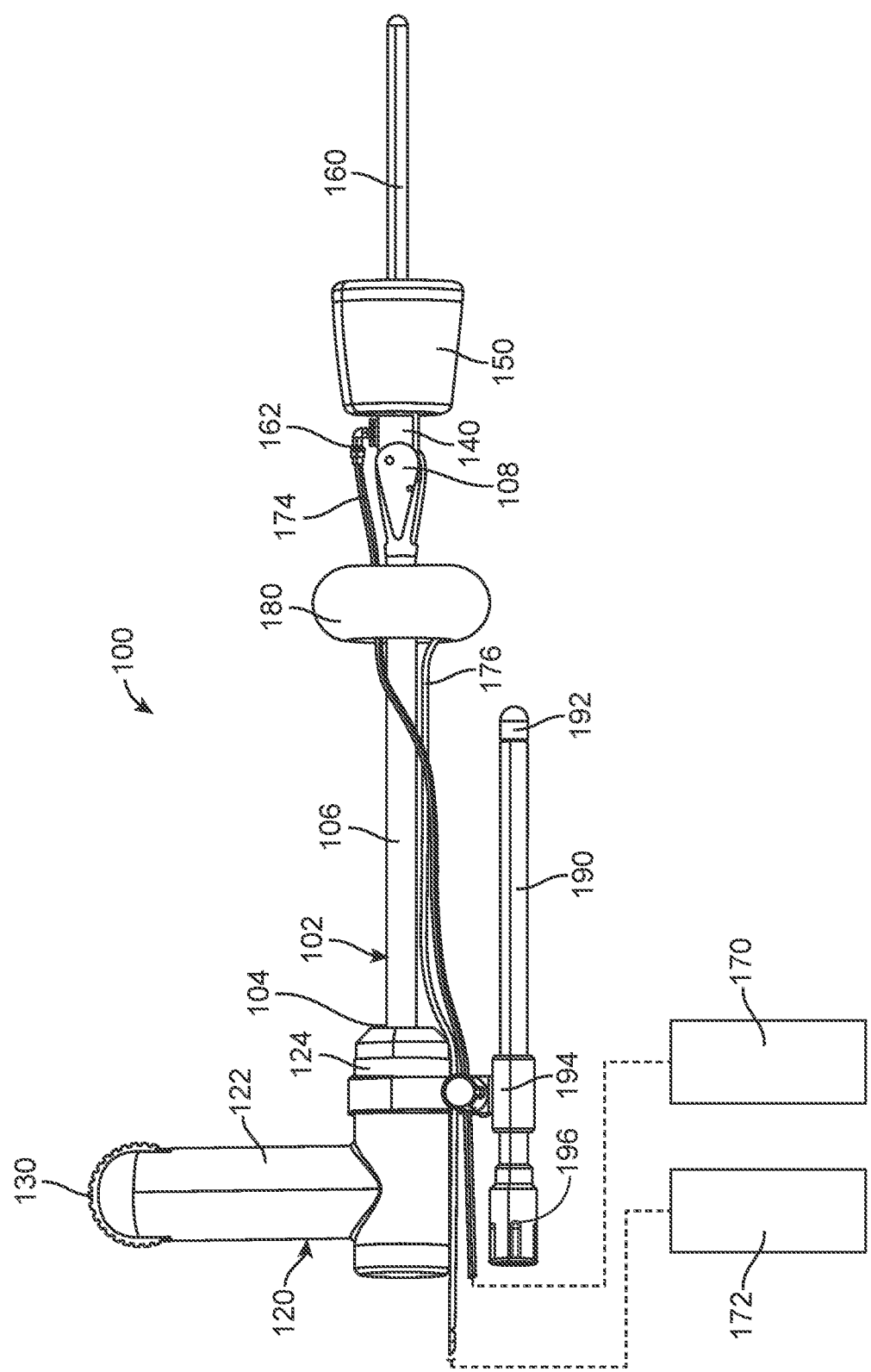
FIG. 1A illustrates an example of a tissue manipulator useful for uterine manipulation.

FIG. 1A illustrates one example of a uterine manipulator 100 in accordance with the methods and devices disclosed herein. As shown, the device 100 includes shaft 102 having a near portion 104, mid portion 106, and far portion 108. The shaft 102 is typically rigid in accordance with known manipulator devices. However, variations include shafts 102 that are slightly flexible or malleable to allow for added maneuverability. Furthermore, the shaft 102 is shown as being straight such that it is uniform about a main axis that runs from the near portion 104 through the mid portion 106 and far portion 108. However, alternate variations of the device can include shafts having a curvature, where the curvature is in a plane, where articulation of the working end (e.g., tip assembly) occurs in the same plane.

As shown, the manipulator 100 includes a handle assembly 120 located on, at or near to the near portion 104 of the shaft 102. In the illustrated variation, the shaft 102 and handle assembly 120 can be affixed a collar. However, any conventional means can be used to join the structures and components of the devices disclosed herein.

The handle assembly 120 includes a stock or grip portion 122 that extends from a main housing 124. The grip portion 122 includes an actuator 130 that controls articulation of an articulating segment 140 discussed below. In the illustrated variation, the actuator comprises a wheel or geared wheel that engages a gearing assembly located within the handle assembly 120. In alternative variations, the actuator can be a lever, smooth wheel, or any other structure that allows performance of the features disclosed below. Turning back to FIG. 1A, the actuator 130 rotates within the same plane as the axis of the shaft 102 as well as the plane in which the articulating segment 140 articulates. The significance of this design is discussed below. The spacing of the actuator from the main handle permits single handed adjustment of the articulating segment, the cup, and the tip assembly while holding the grip portion.

The shaft 102 can include an optional sealing balloon 180 that is coupled to a fluid source 170 via any lumen or similar structure 176. The sealing balloon 180 is shown in an expanded configuration for purposes of illustration. However, during advancement of the device 100 within a body cavity, the balloon 180 will be in a reduced configuration such that it matches, or nearly matches an outer diameter of the shaft 102.

The far portion 108 of the shaft 102 is coupled to an articulating segment 140. As discussed herein the actuator 130 is engaged with a gearing assembly such that when a hand of a user grips the grip portion 122, a thumb or a digit of the hand can rotate (or move) the actuator 130 causing the gearing assembly to articulate the articulating segment 140. A cup 150 (if used) and tip assembly 160, articulate with the articulating segment 140 in either direction away from the main axis. The spacing of the actuator from the main handle permits single handed adjustment of the articulating segment, the cup, and the tip assembly while holding the grip portion. In certain variations, the tip assembly 160 can include a balloon. As shown below, variations of the device 100 include a cup structure 150 that is open at the far end and closed at the near end to define a cavity within the cup. This cavity engages the external os of the uterus when advanced thereagainst. One variation of such a cup structure 150 is a colpotomizer. Alternatively, the cup structure 150 can be replaced with a structure that engages a cervix or the external OS of the uterus, where such alternative structure does not include a cavity.

The tip assembly 160 can also include a port 162 that allows for delivery of a liquid or gas through the tip assembly 160. As shown, the tip assembly 160 is coupled to a fluid source 172 using one or more lumens 174. Therefore, the tip assembly 160 can be used to deliver liquids such as a contrast agent and/or a perfusing fluid such as saline.

The variation disclosed at FIG. 1A also includes a probe device 190 that is coupled to the main housing 124 of the handle 120 via a connecting apparatus 194. The probe device 190 can be positioned along an axis of the shaft 102 to advance/retract the probe relative to the shaft 100. Variations of the device further allow the probe 190 to be rotatable about the main housing 124 and/or articulatable away from the shaft 102. This multi-axis adjustability and rotational ability permits positioning of the probe 190 within secondary adjacent organs (e.g., a rectum) when the tip assembly 160 is used within a main target organ. The probe 192 can include an illumination source anywhere on its surface. As shown, the illumination source 192 can be positioned at distal end. The illumination source can comprise visible light, infrared radiation, or any other form of electromagnetic energy that would allow for detection of the probe from outside of the organ in which it is placed. Moreover, the probe 190 can include a cap 196 or other covering structure to allow for passage of components through the probe 190.

FIG. 1A is intended to show just one variation of the devices disclosed herein. Clearly, variations of the device 100 can be made by those skilled in the art. For example, the lumens 174 176 can extend exterior to the shaft or housing. Alternatively, the lumens 174 176 can extend within the shaft/housing. Variations of the device can omit the tip assembly 160, the cup 150, balloon 180, and/or probe 190 from the device 100 leaving the handle assembly 120, shaft, and articulating segment 140 (where a cup or tip is then attached).

Figure 1B:
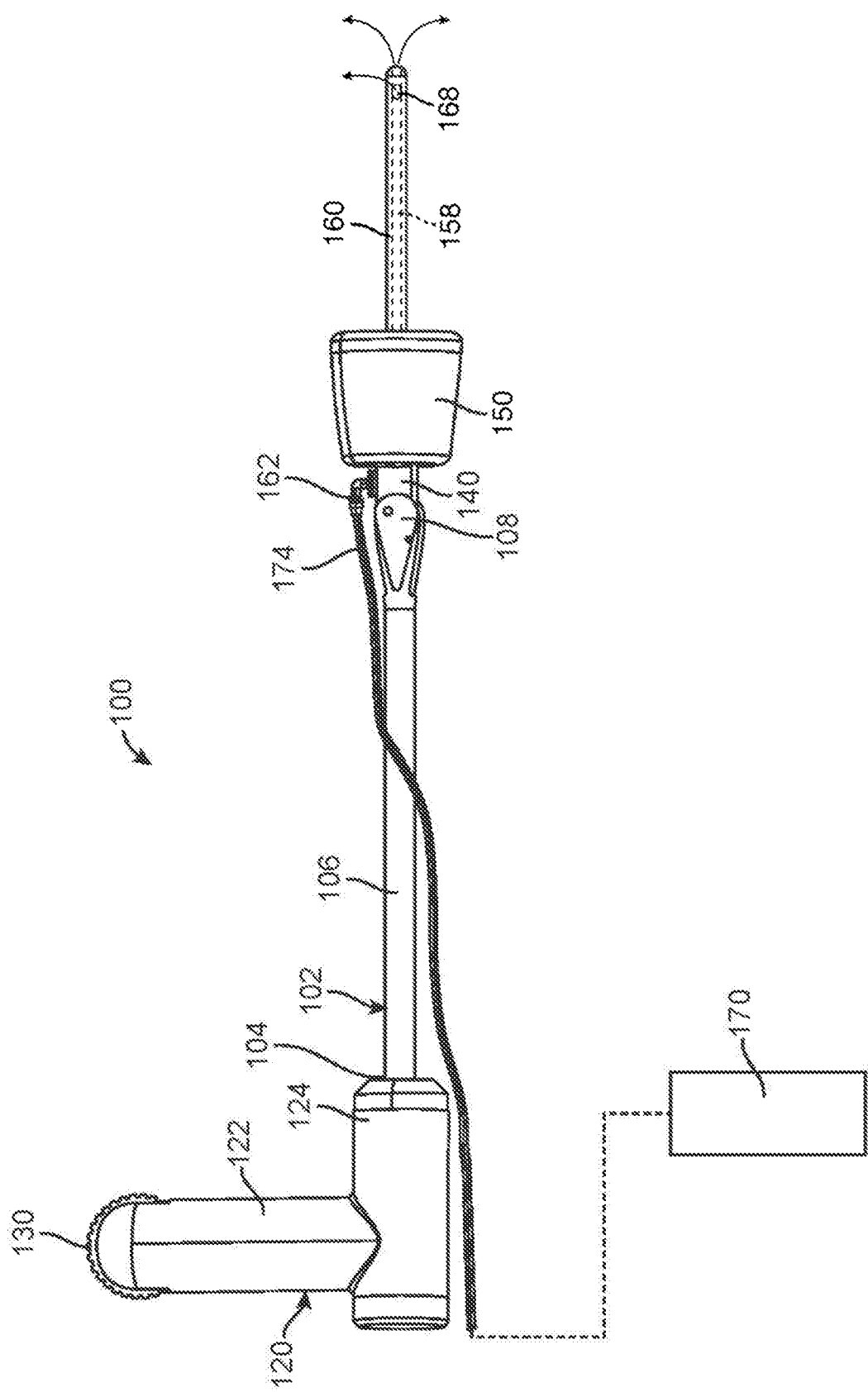
FIG. 1B illustrates another variation of a tissue manipulator useful for uterine manipulation.

FIG. 1B illustrates such an alternate variation of a uterine manipulator device 100 having a handle assembly 120, shaft 102 and an articulating segment 140 coupled to a cup structure 150 with a tip assembly 160 extending therethrough. The illustration also shows a tip assembly 160 having an internal lumen 158 for delivery of fluids (as shown by arrows) either through an end of the tip assembly 160 and/or through one or more ports 168 located laterally to the lumen 158.

Figure 1C:
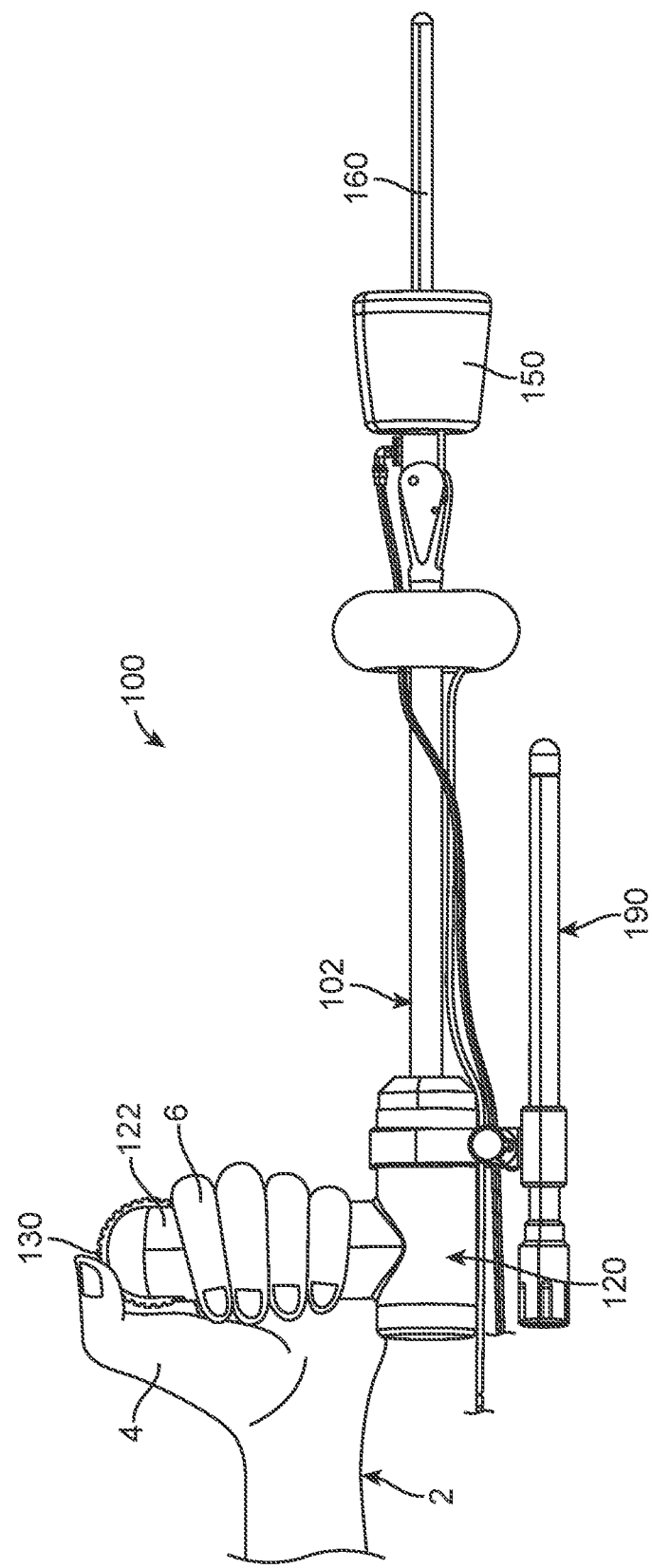
FIG. 1C illustrates an example of a tissue manipulator as described herein that facilitates single handed use to position and articulate a working end of the tissue manipulator.

FIG. 1C illustrates an example of a user's hand 2 as the user positions the device 100. As shown, the handle assembly 120 is configured such that a grip portion 122 extends radially away from a housing 124 of the handle 120. Also, the grip portion 122 and the housing are coupled in axial alignment to the near portion of the shaft 102. This means that all of those components lie in/intersect a plane containing a main axis 110 of the shaft 102. This configuration permits a user's hand 2 to firmly hold or grasp the stock/grip portion 122 while a thumb 4 and/or digit 6 is used to control the actuator 130, which is spaced apart from the housing 124 to an end of the grip portion 122. This positioning allows sufficient space for the user to grasp the grip portion 122 in a natural position. Such a position allows the user to control the device 100 with a wrist of the user being un-flexed. Such a position allows improved control. Furthermore, the ability to securely grasp the grip portion 122 allows a user to keep the device 100 steady while single-handedly adjusting the articulating segment, cup 150, and tip assembly 160.

Figure 2A:
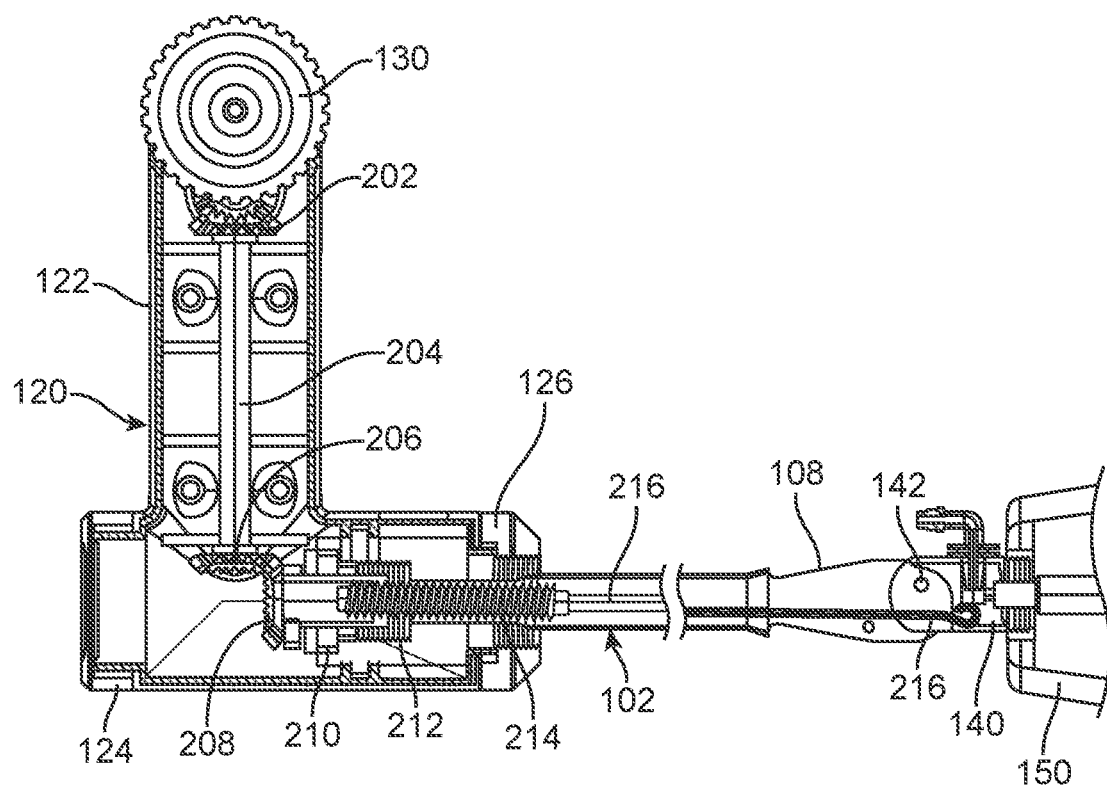
FIG. 2A shows a partial cross-sectional view of a tissue manipulator to illustrate one example of a gearing assembly that causes articulation of a working end of the tissue manipulator device.

FIG. 2A illustrates a cross sectional view of a handle assembly 120, shaft 102, articulating segment 140, and cup structure 150 (partial) to illustrate an example of a gearing assembly that permits articulation of the articulating segment 140, cup 150, and tip assembly. As shown, the actuator 130 can comprise a geared wheel structure that engages a shaft 204 having gear ends 202 206. In an alternate variation, the actuator 130 can be smooth with a gear coupled to a side of the actuator. Rotation of the actuator 130 causes rotation of the shaft 204 such that gear end 206 rotates a driver gear 208 that is part of a worm drive gearing system that transmits the rotational motion of the actuator 130 to linear movement for articulation of the articulating segment 140. The driver gear 208 is positioned within a bearing assembly 210 so that rotation of the driver gear 208 causes a worm gear segment 212 of the driver gear to translate a worm drive 214 in an axial direction relative to the shaft 102. The worm drive 214 is coupled to a linkage 216 that extends to a pivot structure (e.g., a pin) on the articulating segment 140. Therefore, rotational movement of the actuator 130 causes axial movement of the worm gear 214 and linkage 216 so that articulating segment pivots about pivot point 142 to cause movement of the articulating segment 140 away from an axis of the shaft 102. In this illustrated configuration, the actuator 130 rotates in a plane that intersects an axis of the shaft 102. It is noted that the manual gearing assembly can also include electronic motors or servo motors in place of the manually operated gearing. In such a case, the gear assembly would require a switch and power supply to initiate movement of the articulating segment.

Figure 2B:
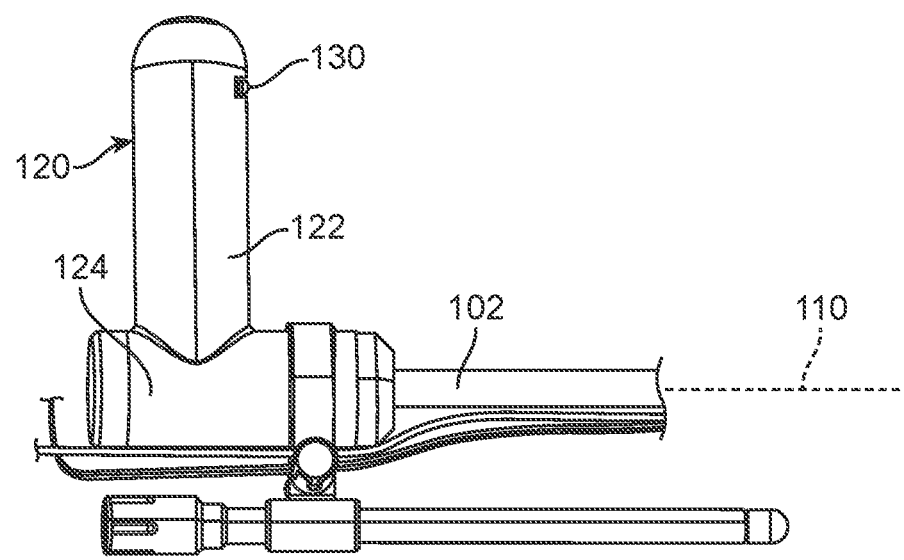
FIG. 2B shows a partial view of another variation of a tissue manipulator device where an actuator is positioned within a grip portion of a handle.

FIG. 2B illustrates another variation of a device where the actuator 130 rotates in a plane that does not intersect an axis 110 of the shaft 102. In this variation, the actuator 130 is positioned within the grip portion and rotates parallel to a gear end 202 of the gearing assembly (in an alternate variation, the actuator can be a part of the gear end). The variation illustrated in FIG. 2B simply provides an alternate design of the device while providing the benefits described herein. As noted above, variations of the device contemplate an actuator that is a lever rather than a wheel structure.

Figure 3A:
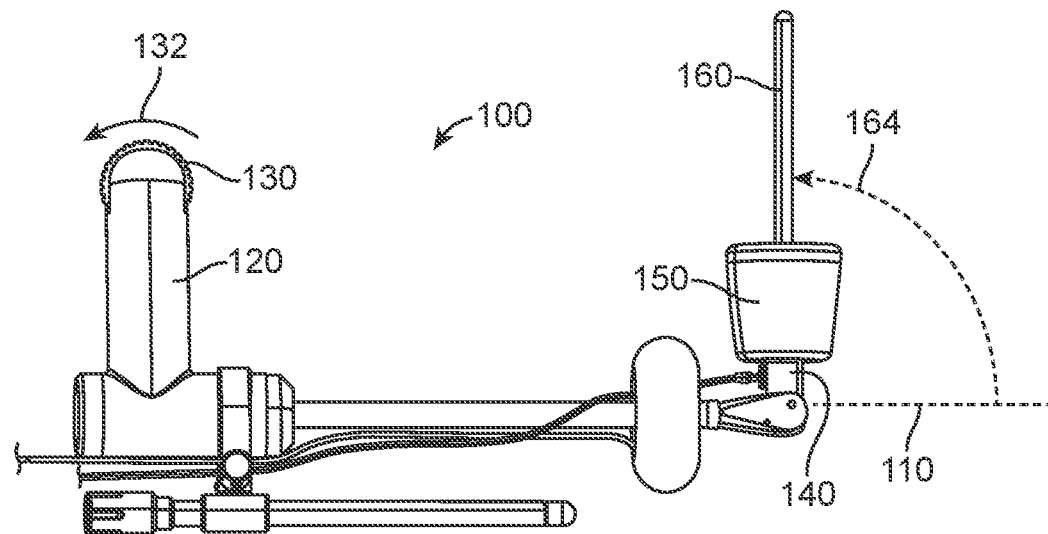
FIGS. 3A and 3B show an example of articulation of a working end of a manipulator device as described herein.
Figure 3B:
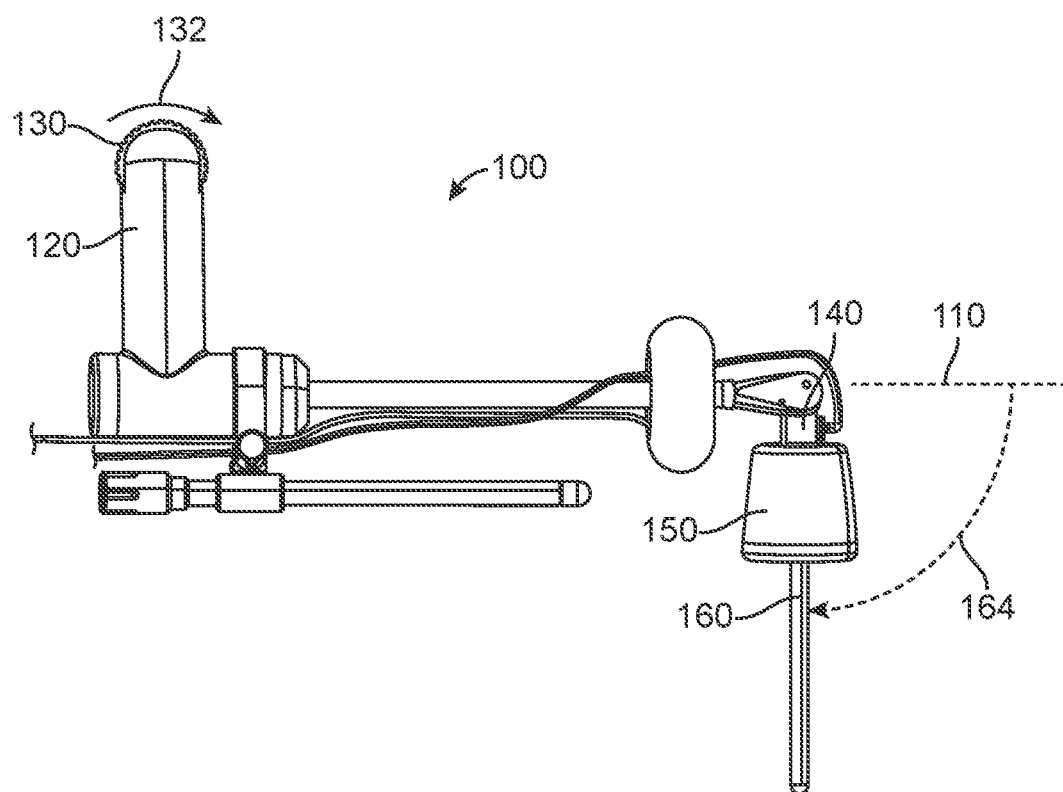

FIGS. 3A and 3B illustrate movement or articulation of the articulating segment 140 in response to movement of actuator 132. As discussed above, movement 132 of the actuator 130 causes a gearing assembly to articulate the articulating segment 140 such that the articulating segment 140 moves away from a main axis 110 of the shaft of the device 100. In one variation, the device 100 is configured to span +90 degrees to −90 degrees (as measured relative to the main axis 110). This span is shown respectively in FIG. 3A (+90) and FIG. 3B (−90). Therefore, the device 100 permits up to 180 degrees of deflection of the articulating segment 140, cup structure 150 and tip assembly. Alternate variations of the device can produce greater or less deflection, as well as deflection that is not symmetric relative to the axis (e.g. +120 degrees and −60 degrees) The direction of rotation 132 shown in FIGS. 3A and 3B can be reverse. For example, as shown, counter-clockwise rotation of the actuator (FIG. 3A) could produce movement of the articulating segment 140 in a counter clockwise arc (FIG. 3A) and likewise, clockwise rotation of the actuator (FIG. 3B) could produce movement of the articulating segment 140 in a clockwise arc (FIG. 3B). In alternate variations, counter clockwise rotation of the actuator could produce clockwise rotation of the articulating segment, while clockwise rotation of the actuator could produce counter clockwise rotation of the articulating segment FIGS. 4A to 4D provide an illustration of a procedure in which the uterine manipulation device 100 is used to reposition a uterus 12 within an abdominopelvic cavity 10. The illustrations are intended to convey an understanding of the methods and use of the device rather than provide a true anatomic representation of the organs. Furthermore, as noted above, the uterine manipulation device 100 can be used by entering through a natural body passage (in this case the vaginal passage 14), in an open surgical procedure, or through an artificially created port.

Figure 4A:
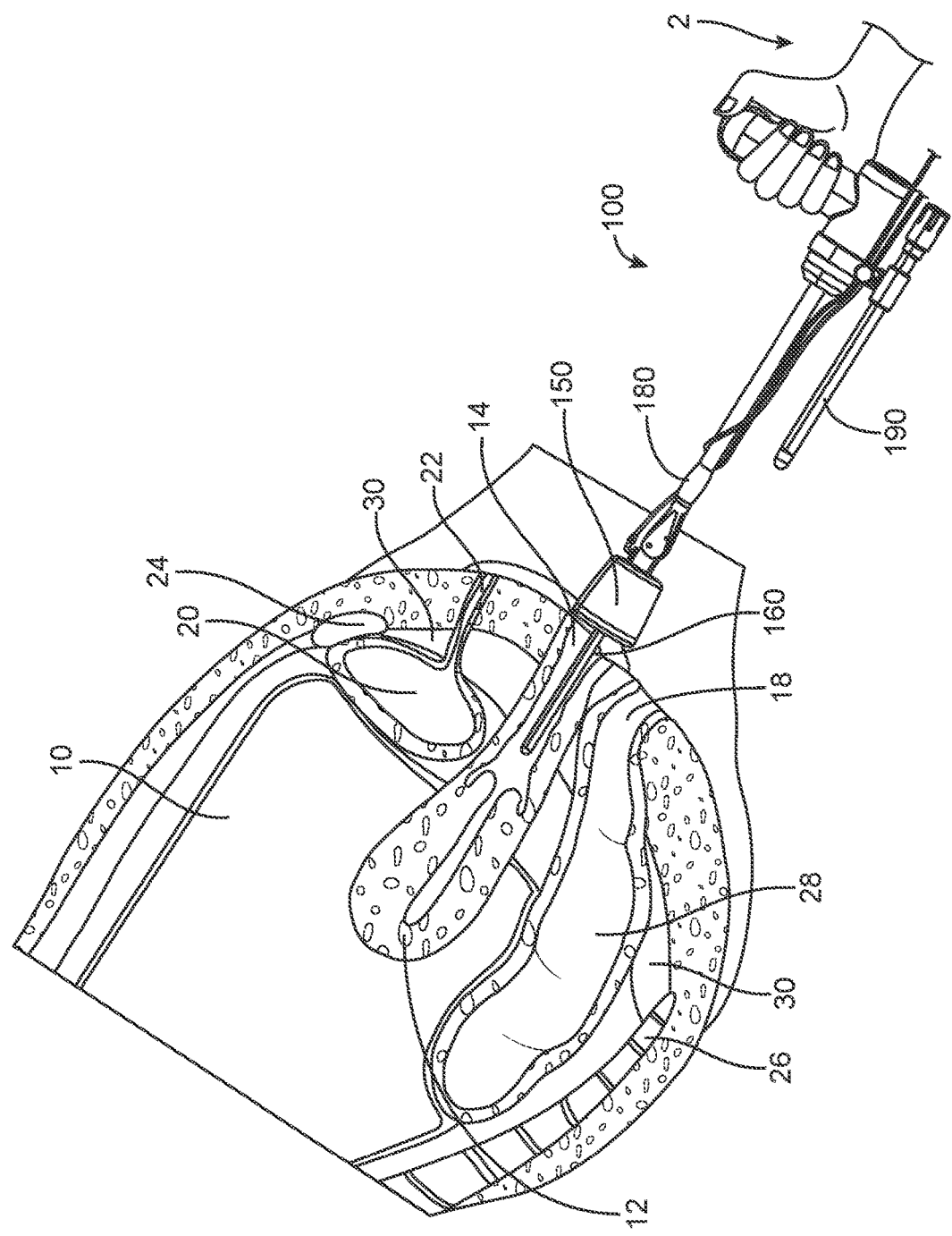
FIG. 4A illustrates a uterine manipulation device having a tip assembly that is advanced into a vagina.

FIG. 4A illustrates a uterine manipulation device 100 having a tip assembly 160 that is advanced into a vagina 14. As shown, the caregiver can maneuver the device 100 using a single hand 2 while an axis of the shaft of the device is aligned with the vaginal passage 14. As noted above, it is important to ensure that the adjacent organs are not damaged. Therefore, a probe 190 attached to the manipulation device 100 can be aligned independently from the tip assembly 160 and cup structure 150 such that the probe enters at an anus 18 of the rectum 28. The illustration also shows the bladder 20, urethra 22, pubic bone 24, coccyx 26, and pelvic floor muscles 30.

Figure 4B:
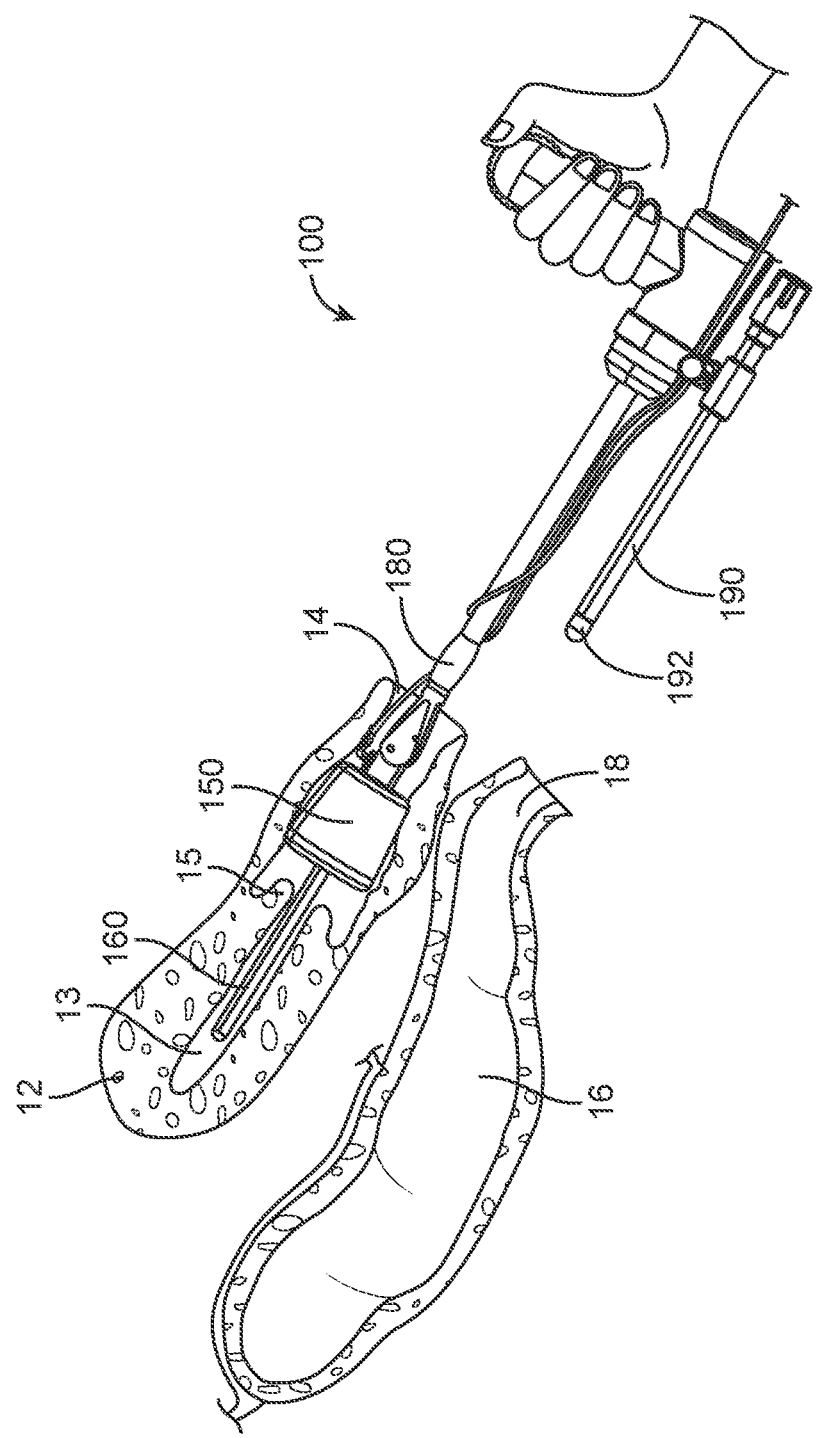
FIG. 4B illustrates advancement of the cup structure within the vagina and advanced towards the cervix.
Figure 4C:
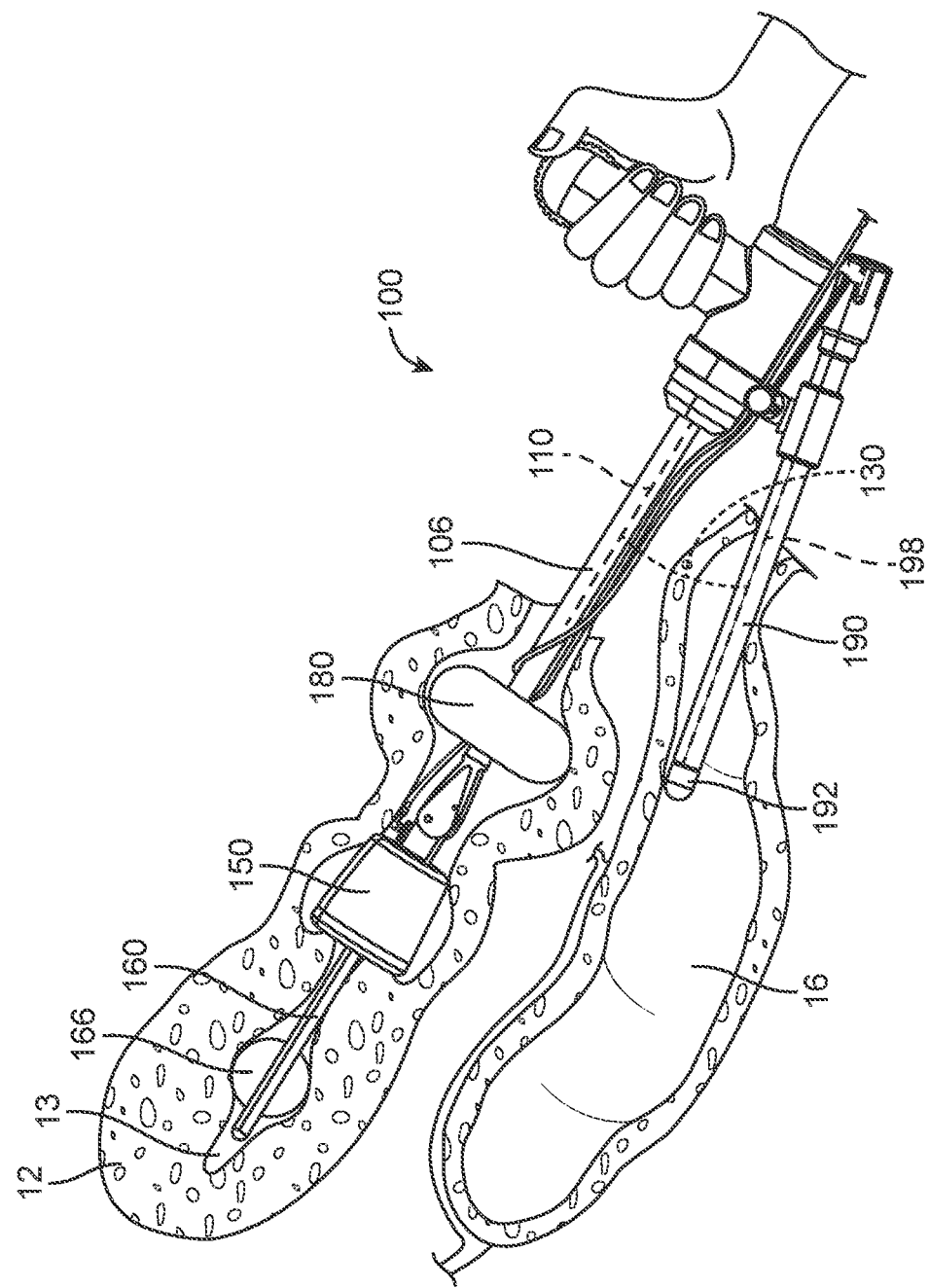
FIG. 4C illustrates the state where the working end of the device is positioned within the patient as the tip assembly is positioned within the uterine cavity and the cup structure receives the cervix.
Figure 4D:
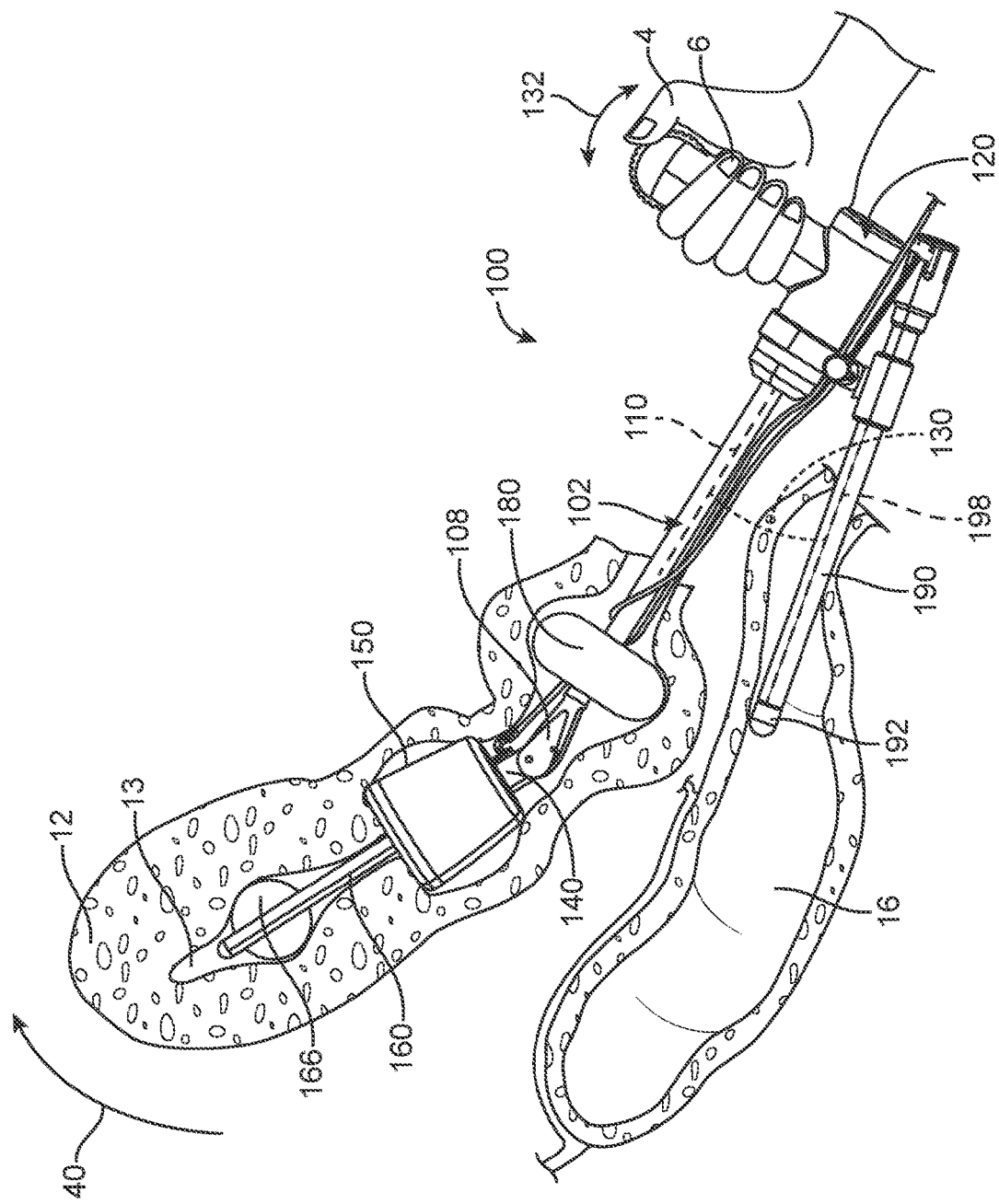
FIG. 4D illustrates movement of the actuator in either direction using a thumb or a digit of the hand of a user to articulate a working end of a tissue manipulation device.

For convenience, FIGS. 4B to 4D only illustrate the uterus 12 and rectum 16. FIG. 4B illustrates advancement of the cup structure 150 within the vagina 14 and advanced towards the cervix. As shown, the device 100 can include one or more sealing balloons 180 that, prior to entering the body, are in a deflated configuration.

FIG. 4C illustrates the state where the working end of the device 100 is positioned within the patient as the tip assembly 160 is positioned within the uterine cavity 14 and the cup structure 150 receives the cervix (not shown in FIG. 4C). At this point, the operator can inflate a sealing balloon 180 (if one is used), to seal the vaginal passage. FIG. 4C also illustrates an optional secondary balloon 166 that is commonly used during these procedures. Such a balloon 166 is inflated within the uterine cavity 13 to assist in manipulation of the cavity 13.

FIG. 4C also illustrates the probe 190 as being positioned within the rectum 16. As discussed above, the probe can include one or more illumination sources 192 that allows the physician to identify the surface of the adjacent rectum, which reduces the chances that the rectum 16 will be inadvertently punctured. The probe 190 is coupled to the device 100 (as discussed above), such that the operator can manipulate the probe in a number of directions. For example, the probe can be advanced/retracted in a direction that is parallel to the shaft 102. The probe 190 can be rotated about the handle 120. Also, the probe 190 can be pivoted relative to a main axis 110 of the shaft (illustrated by angle 130, which is the angle between a main axis 110 of the shaft 102 and an axis 198 of the probe 190).

FIG. 4D illustrates movement of the actuator in either direction 132 using a thumb or a digit 6 of the hand of a user. As discussed above, the handle 120 of the device 100 can remain stationary while the articulating portion 160, cup structure 150, and secondary balloon 160 move in an arc at the far end 108 of the shaft 102 as shown by arrow 40, which moves the uterus 12 within the abdominopelvic cavity.

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Various changes may be made to the invention described. For example, the invention includes combinations of aspects of the variations of the devices described herein as well as the combination of the variations themselves. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

It is important to note that where possible, aspects of the various described embodiments, or the embodiments themselves can be combined. Where such combinations are intended to be within the scope of this disclosure.

We claim:

1. A uterine manipulator comprising:
a shaft having a far-portion, a near-portion, and a mid-portion extending therebetween, the shaft having a main axis;
a handle assembly comprising a housing and a grip portion, the housing coupled in axial alignment to the near portion of the shaft, where the grip portion extends radially away from the housing;
an articulating segment coupled to the far portion of the shaft;
a gearing assembly located within the handle assembly and coupled to the articulating segment, wherein actuation of the gearing assembly causes articulation of the articulating segment;
a cup structure having an open end located distally to a closed end, the closed end removably attached to the articulating segment;
a tip assembly coupled to the articulating segment and extending distally through the cup structure; and
an actuator coupled to the grip portion and spaced from the housing, the actuator engaged with the gearing assembly such that when a hand of a user grips the grip portion, a thumb or a digit of the hand can rotate or move the actuator causing the gearing assembly to articulate the articulating segment, the cup, and the tip assembly away from the main axis, and where the spacing of the actuator from the main handle permits single handed adjustment of the articulating segment, the cup, and the tip assembly while holding the grip portion.

2. The uterine manipulator of claim 1, further comprising a balloon device positioned at a far portion of the shaft.

3. The uterine manipulator of claim 1, further comprising a rectal probe adjustably coupled to the housing of the handle assembly such that manipulation of the grip portion allows manipulation of the rectal probe.

4. The uterine manipulator of claim 3, wherein the rectal probe is adjustable axially and rotationally relative to the main housing.

5. The uterine manipulator of claim 3, wherein the rectal probe is angularly adjustable relative to the main axis of the shaft.

6. The uterine manipulator of claim 3, wherein the rectal probe comprises an illumination source at a distal end.

7. The uterine manipulator of claim 1, wherein the gearing assembly is configured to articulate the articulating segment within an arc of at least 180 degrees relative to the main axis.

8. The uterine manipulator of claim 1, wherein the tip assembly comprises a lumen to permit delivery of a fluid through the tip assembly.

9. The uterine manipulator of claim 8, further comprising a fluid port in fluid communication with the lumen, wherein the fluid port is coupled to a source lumen that is configured to fluidly couple to a fluid supply.

10. The uterine manipulator of claim 9, where the fluid supply comprises a contrast fluid.

11. The uterine manipulator of claim 1, further comprising a plurality of cup structures of varying sizes, where each of the cup structures is removably coupleable to the articulating segment.

12. The uterine manipulator of claim 1, wherein the cup structure comprises a colpotomizer.

13. The uterine manipulator of claim 1, wherein the shaft is rigid and straight.

14. The uterine manipulator of claim 13, wherein the grip portion forms an angle of 180 degrees relative to the main axis.

15. The uterine manipulator of claim 1, wherein the actuator comprises a wheel structure.

16. The uterine manipulator of claim 15, wherein the wheel structure comprises a cogwheel.

17. The uterine manipulator of claim 15, wherein the wheel structure is rotatable in a plane containing the main axis.

18. The uterine manipulator of claim 15, where the wheel structure is rotatable in a plane offset from a plane containing the main axis.

19. A uterine manipulator comprising:
   a shaft having a far-portion, a near-portion, and a mid-portion extending therebetween, the shaft having a main axis;
   a handle assembly comprising a housing and a grip portion, the housing coupled in axial alignment to the near portion of the shaft, where the grip portion extends radially away from the housing;
   a rectal probe adjustably coupled to the housing of the handle assembly such that manipulation of the grip portion allows manipulation of the rectal probe;
   a balloon device positioned at a far portion of the shaft;
   an articulating segment coupled to the far portion of the shaft;
   a gearing assembly located within the handle assembly and coupled to the articulating segment, wherein actuation of the gearing assembly causes articulation of the articulating segment;
   a cup structure having an open end located distally to a closed end, the closed end removably attached to the articulating segment;
   a tip assembly coupled to the articulating segment and extending distally through the cup structure; and
   an actuator coupled to the grip portion and spaced from the main handle portion, the actuator engaged with the gearing assembly such that when a hand of a user grips the grip portion, a thumb or a digit of the hand can rotate or move the actuator causing the gearing assembly to articulate the articulating segment, the cup, and the tip assembly away from the main axis, and where the spacing of the actuator from the main handle permits single handed adjustment of the articulating segment, the cup, and the tip assembly while holding the grip portion.

* * * * *

UNITED STATES PATENT AND TRADEMARK OFFICE
CERTIFICATE OF CORRECTION

PATENT NO. : 10,820,926 B1
APPLICATION NO. : 16/588214
DATED : November 3, 2020
INVENTOR(S) : José Gerardo Garza Leal et al.

Page 1 of 1

It is certified that error appears in the above-identified patent and that said Letters Patent is hereby corrected as shown below:

On the Title Page

Column 1, Add Item (30):
--Foreign Application Priority Data
MX/u/2019/000324 filed July 5, 2019--

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*